(12) United States Patent
Burns

(10) Patent No.: US 7,007,689 B2
(45) Date of Patent: Mar. 7, 2006

(54) INHALATION DEVICE

(75) Inventor: Stephen Burns, Derby (GB)

(73) Assignee: AstraZeneca AB, Sodertalje (SE)

( * ) Notice: Subject to any disclaimer, the term of this patent is extended or adjusted under 35 U.S.C. 154(b) by 145 days.

(21) Appl. No.: 10/698,942

(22) Filed: Nov. 3, 2003

(65) Prior Publication Data

US 2004/0134489 A1 Jul. 15, 2004

Related U.S. Application Data

(63) Continuation of application No. 09/840,875, filed on Apr. 25, 2001, now abandoned, which is a continuation of application No. 09/380,294, filed as application No. PCT/SE99/01198 on Jul. 3, 1999, now abandoned.

(30) Foreign Application Priority Data

Jul. 1, 1999 (SE) .................. 9802398

(51) Int. Cl.
A61M 11/00 (2006.01)

(52) U.S. Cl. .......... 128/200.23; 128/200.14; 128/200.24

(58) Field of Classification Search .............
128/200.14–200.24, 203.23, 207.14–207.18
See application file for complete search history.

(56) References Cited

U.S. PATENT DOCUMENTS

| 5,447,150 | A |   | 9/1995  | Bacon                         |
|-----------|---|---|---------|-------------------------------|
| 5,460,171 | A | * | 10/1995 | Pesenti et al. ...... 128/200.23 |
| 5,520,166 | A |   | 5/1996  | Ritson et al.                 |
| 5,598,836 | A |   | 2/1997  | Larson et al.                 |
| 5,860,416 | A |   | 1/1999  | Howlett                       |
| 5,899,201 | A | * | 5/1999  | Schultz et al. ...... 128/200.23 |
| 6,305,371 | B1|   | 10/2001 | Frid et al.                   |

FOREIGN PATENT DOCUMENTS

| DE | 24 35 186 | 2/1975 |
| DE | 2435186 A1 | 2/1976 |
| EP | 0 808 635 A2 | 11/1997 |
| WO | 95/24234 | 9/1995 |
| WO | WO 95/24234 | 9/1995 |
| WO | 99/94740 | 2/1999 |
| WO | WO 99/04840 | 2/1999 |

* cited by examiner

Primary Examiner—Glenn K. Dawson
(74) Attorney, Agent, or Firm—Nixon & Vanderhye

(57) ABSTRACT

An actuator for a pressurised metered dose inhaler, including: a tubular section (38) providing an outlet through which medicament is in use inhaled; and a nozzle block (42) including a tubular element (44) having a free end over which the valve stem (14) of a canister (2) is in use located and a spray orifice (50) in fluid communication with the tubular element (44) for directing a spray into the tubular section (38).

8 Claims, 2 Drawing Sheets

INHALATION DEVICE

This application is a continuation of Application Ser. No. 09/840,875, filed Apr. 25, 2001, now abandoned which is a continuation of 09/380,294, filed Aug. 31, 1999, now abandoned, which is a National Phase under 35 U.S.C. §371 of PCT/SE99/01198, filed Jul. 3, 1999, the entire content of which is hereby incorporated by reference in this application.

The present invention relates to an actuator for a pressurised metered dose inhaler and a pressurised metered dose inhaler including the same.

BACKGROUND OF THE INVENTION

In using conventional pressurised metered dose inhalers with some hydrofluoroalkane (HFA) formulations being developed by the applicant company it has been found that medicament tends to deposit in the valve stems of the canisters thereof. It will be appreciated that this deposition could lead to the user receiving an unusually high dose of medicament if the deposit were at least in part to break away or, indeed, result in the valve stems becoming blocked, thereby rendering the pressurised metered dose inhalers inoperative. Ideally, one would simply just wash the canisters to remove the deposit. Unfortunately, however, it is not possible to wash the canisters as the formulations are sensitive to moisture and would as a result of washing be contaminated.

SUMMARY OF THE INVENTION

Accordingly, the present invention provides an actuator for a pressurised metered dose inhaler, including: a tubular section providing an outlet through which medicament is in use inhaled; and a nozzle block including a tubular element having a free end over which the valve stem of a canister is in use located and a spray orifice in fluid communication with the tubular element for directing a spray into the tubular section.

By providing the nozzle block of the actuator with a tubular element over which the valve stem of a canister is located, medicament will deposit on the inner radial surface of the tubular element and not in the valve stem of the canister. In this way, the user is able to prevent the build up of any appreciable amount of deposit by washing the actuator regularly: the actuator being washable when separated from the canister.

Preferably, the tubular element is configured such that an outer radial surface thereof is a close fit with an inner radial surface of the valve stem of the canister.

More preferably, the tubular element is configured such that an outer radial surface thereof is a tight fit with an inner radial surface of the valve stem of the canister.

Preferably, the tubular element is of circular section.

Preferably, the nozzle block includes an abutment against which in use bears the distal end of the valve stem of the canister.

More preferably, the abutment comprises a surface which extends radially outwardly of the tubular element.

In a preferred embodiment the nozzle block includes a further tubular element co-axial with the first-mentioned tubular element such that the tubular elements define an annular channel in which the valve stem of the canister is in use located.

Preferably, the further tubular element is configured such that an inner radial surface thereof is a close fit with an outer radial surface of the valve stem of the canister.

More preferably, the further tubular element is configured such that an inner radial surface thereof is a tight fit with an outer radial surface of the valve stem of the canister.

Preferably, the further tubular element is of circular section.

The present invention also extends to a pressurised metered dose inhaler comprising the above-described actuator and a canister including a valve stem extending therefrom.

BRIEF DESCRIPTION OF THE DRAWINGS

A preferred embodiment of the present invention will now be described hereinbelow by way of example only with reference to the accompanying drawings, in which.

Figure 1:
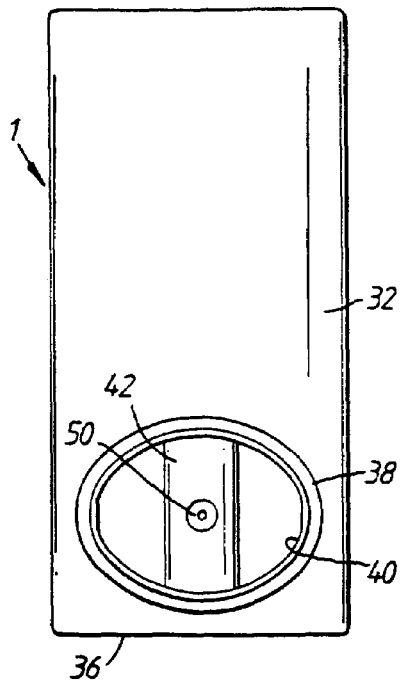
FIG. 1 illustrates a front view of an actuator of a pressurised metered dose inhaler in accordance with a preferred embodiment of the present invention.
Figure 2:
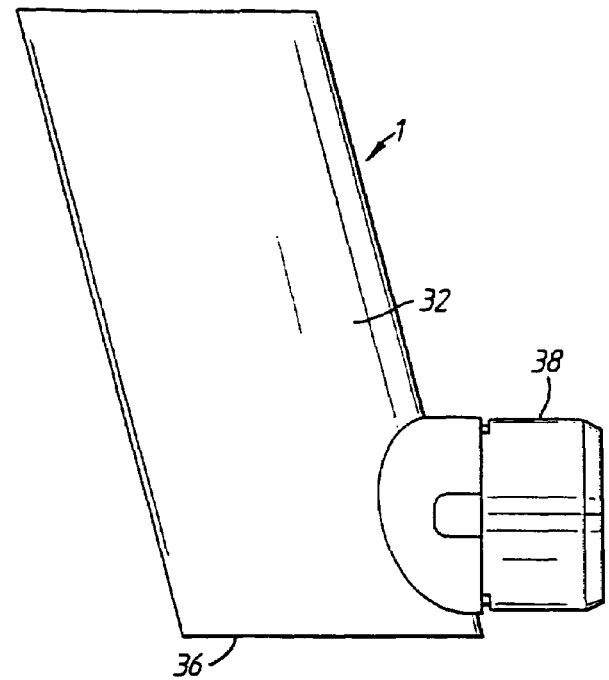
FIG. 2 illustrates a side view of the actuator of FIG. 1.
Figure 3:
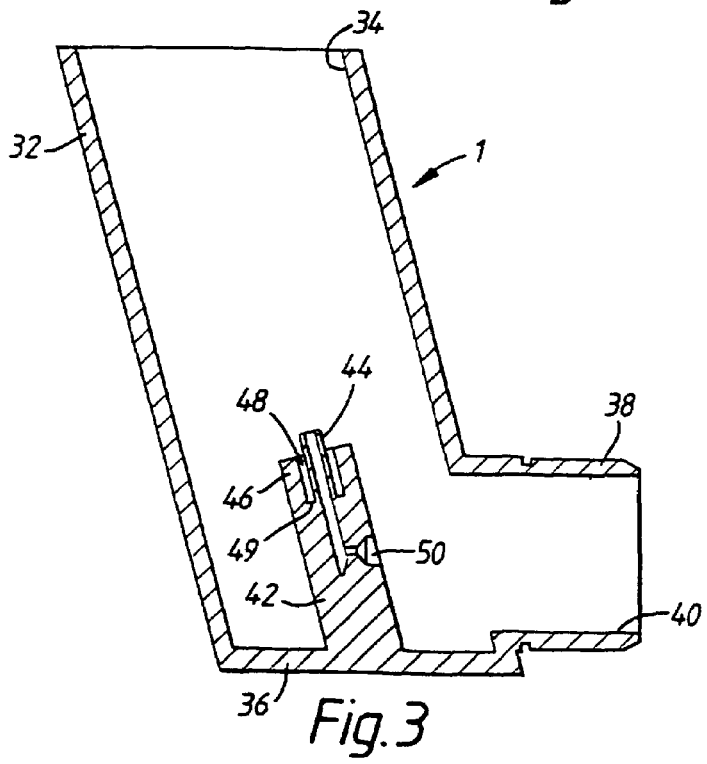
FIG. 3 illustrates a vertical sectional view of the actuator of FIG. 1.
Figure 4:
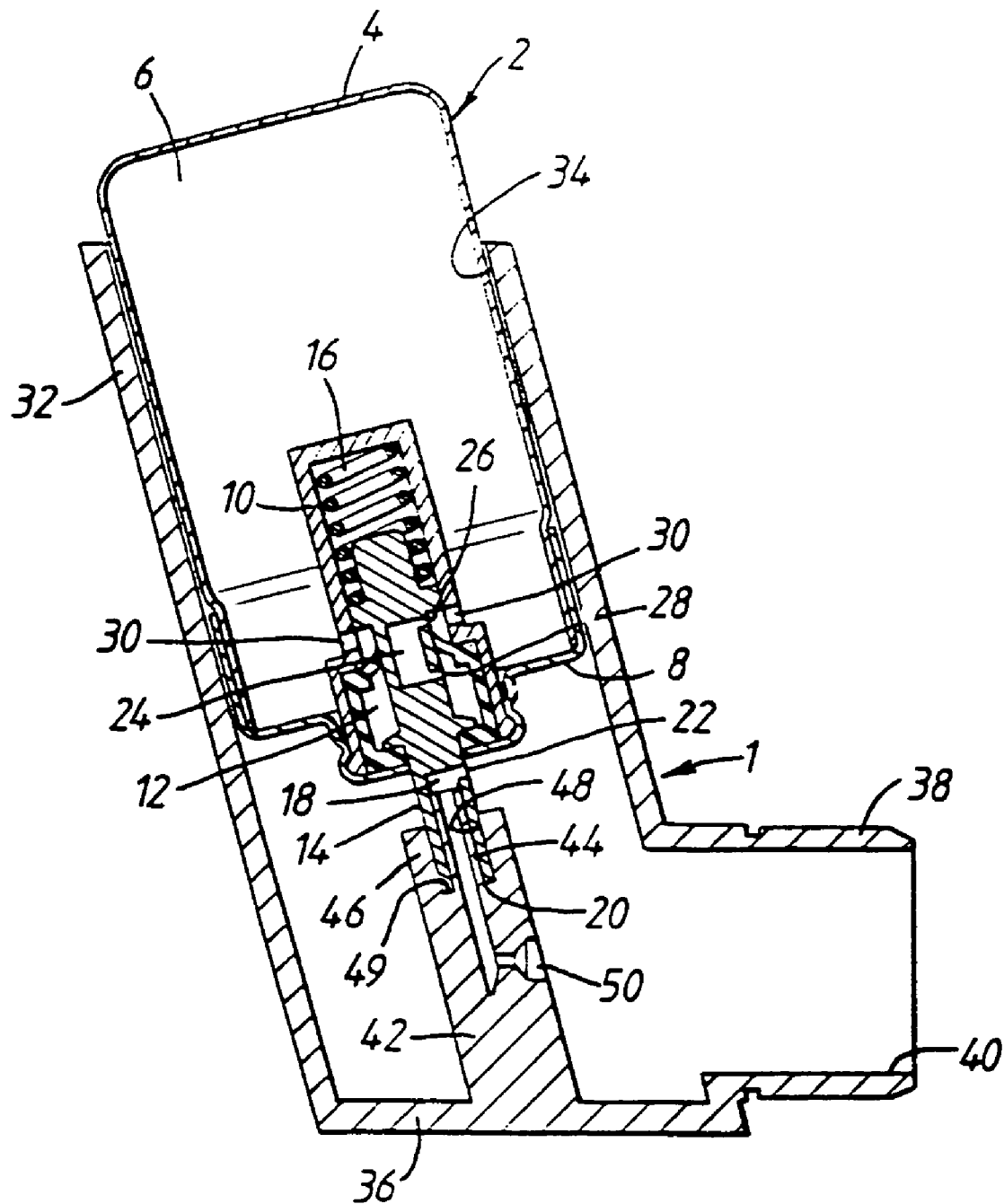
FIG. 4 illustrates a vertical sectional view of the pressurised metered dose inhaler of the preferred embodiment of the present invention.

The pressurised metered dose inhaler comprises an actuator 1 and an aerosol canister 2 fitted therein.

DETAILED DESCRIPTION OF PREFERRED EMBODIMENTS

The canister 2 comprises a body 4 which defines a storage chamber 6 for holding a suspension or solution of a medicament in a propellant under pressure. The body 4 includes a head 8 which includes a housing 10 that defines a metering chamber 12 and a valve stem 14 that is movably disposed in the housing 10 and extends from the head 8. The valve stem 14 is movable between an extended, closed position (as illustrated) and a depressed, open position (not illustrated), the valve stem 14 normally being biased by a compression spring 16 disposed in the housing 10 into the closed position. The valve stem 14 includes a first conduit 18 which includes a first, outlet opening 20 located at the distal end of the valve stem 14 and a second, inlet opening 22 located in the side wall of the valve stem 14. The valve stem 14 further includes a second conduit 24 in that part thereof which is always disposed within the body 4. The second conduit 24 includes first and second axially-spaced openings 26, 28 located in the side wall of the valve stem 14 and enables communication between the storage chamber 6 and the metering chamber 12 via bores 30 in the housing 10. In this regard, it will be noted that the structure of the metering chamber 12 and the valve stem 14 of the canister 2 is known per se.

The actuator 1 comprises a first, main tubular section 32, one, the upper, end of which is open and provides an opening 34 into which the canister 2 is in use inserted and the other, lower, end of which is closed by a wall member 36. The actuator 1 further comprises a second tubular section 38 which extends substantially laterally from the other, that is, the lower, end of the main tubular section 32; the second tubular section 38 acting as a mouthpiece which is in use gripped in the lips of a user and including an opening 40 at the distal end thereof through which medicament is in use inhaled. The actuator 1 still further comprises a nozzle block 42 which extends upwardly from the wall member 36 into the main tubular section 32. The nozzle block 42 includes a first tubular element 4, in this embodiment of circular section, over which the valve stem 14 of the canister 2 is located. The first tubular element 44 is configured such that the radial dimension of the outer radial surface thereof is a close fit with the inner radial surface of the first conduit 18 in the valve stem 14. In this way, no appreciable amount of medicament can build up between the outer radial surface of the first tubular element 44 and the inner radial surface of the first conduit 18 in the valve stem 14. In a preferred embodiment the first tubular element 44 is configured such that the radial dimension of the outer radial surface thereof is a tight fit with the inner radial surface of the first conduit 18 in the valve stem 14. In this way, material cannot escape between the outer radial surface of the first tubular element 44 and the inner radial surface of the first conduit 18 in the valve stem 14. The first tubular element 44 is further configured to be of such a length as to extend within the first conduit 18 in the valve stem 14 to a position adjacent that part of the second opening 22 in the valve stem 14 which is axially closest to distal end of the valve stem 14. In this way, the second opening 22 in the valve stem 14 is always open. The first tubular element 44 is located on the longitudinal axis of the main tubular section 32. In this way, the valve stem 14 will always be aligned with the first tubular element 44 on insertion of the canister 2 into the actuator 1, thereby allowing easy fitting and removal. The nozzle block 42 further includes a second tubular element 46, in this embodiment also of circular section, which is co-axial with the first tubular element 44 and is disposed such that the outer radial surface of the first tubular element 44 and the inner radial surface of the second tubular element 46 define an annular channel 48, the bottom surface 49 of which provides an abutment for the distal end of the valve stem 14. The second tubular element 46 is configured such that the radial dimension of the inner radial surface thereof is a close fit with the outer radial surface of the valve stem 14. In this way, lateral movement of the valve stem 14 is prevented, thereby ensuring that the first tubular element 44 cannot be damaged by such lateral movement of the valve stem 14. In a preferred embodiment the second tubular element 46 is configured such that the radial dimension of the inner radial surface thereof is a tight fit with the outer radial surface of the valve stem 14. In this way, material cannot escape between the outer radial surface of the valve stem 14 and the inner radial surface of the second tubular element 46. The nozzle block 42 still further includes a laterally-directed spray orifice 50 which is in fluid communication with the first tubular element 44 and configured to direct a spray into the second tubular section 38 acting as the mouthpiece.

In use, a user grips the mouthpiece provided by the second tubular section 38 in the lips. The user then depresses the base of the body 4 of the canister 2 which extends out of the opening 34 in the main tubular section 32 so as to release a dose of medicament from the canister 2 and at the same time inhales so as to inhale the dose of medicament.

In this embodiment the actuator 1 is formed entirely of a plastics material, typically by moulding. In an alternative embodiment the first tubular element 44 could be provided by a preformed thin-walled metal tube, such as a stainless steel tube, to which is fitted or moulded a component providing the remainder of the actuator 1.

Finally, it will be understood that the present invention has been described in its preferred embodiment and can be modified in many different ways without departing from the scope of the invention as defined by the appended claims.

What is claimed is:

1. An actuator for a pressurised metered dose inhaler, comprising:
   a tubular section providing an outlet through which medicament is in use inhaled;
   a nozzle block having a first tubular element with an outer radial surface and a free end and a second tubular element having an inner radial surface, said first and second tubular elements being co-axial with each other, said outer and inner radial surfaces being spaced from each other to define an annular space between said inner and outer radial surfaces, wherein in use a valve stem of a canister is located over the free end of the first tubular element and in said annular space; and
   a spray orifice in fluid communication with said first tubular element for directing a spray into the tubular section.

2. The actuator of claim 1, wherein the first tubular element is of circular section.

3. The actuator of claim 1, wherein the nozzle block includes an abutment against which in use bears a distal end of the valve stem of the canister.

4. The actuator of claim 3, wherein the first abutment comprises a surface which extends radially outwardly of the tubular element.

5. The actuator of claim 1, wherein the inner radial surface of said second tubular element is a close fit with an outer radial surface of the valve stem of the canister.

6. The actuator of claim 1, wherein the inner radial surface of said second tubular element is a tight fit with an outer radial surface of the valve stem of the canister.

7. The actuator of claim 1, wherein the second tubular element is of circular section.

8. A pressurised metered dose inhaler comprising the actuator of claim 1 and a canister including a valve stem extending therefrom.

* * * * *

UNITED STATES PATENT AND TRADEMARK OFFICE
CERTIFICATE OF CORRECTION

PATENT NO. : 7,007,689 B2
APPLICATION NO. : 10/698942
DATED : March 7, 2006
INVENTOR(S) : Stephen Burns It is certified that error appears in the above-identified patent and that said Letters Patent is hereby corrected as shown below:

Title page of the patent, left hand column (63) "Related U.S. Application Data", please delete "which is a continuation of application No. 09/380,294, filed as application No. PCT/SE99/01198 on Jul. 3, 1999, now abandoned." and insert --which is a continuation of application No. 09/380,294, filed August 31, 1999, now abandoned, which is a National Phase under 35 U.S.C. §371 of PCT/SE99/01198 filed on Jul. 1, 1999, now abandoned.--.

Title page of the patent, left hand column (30) "Foreign Application Priority Data", please delete "Jul. 1, 1999 (SE) 9802398" and insert --Jul. 3, 1998 (SE) 9802398-9--

Signed and Sealed this

Fifteenth Day of April, 2008

JON W. DUDAS
*Director of the United States Patent and Trademark Office*